(12) United States Patent
Nötzel et al.

(10) Patent No.: US 9,549,269 B2
(45) Date of Patent: Jan. 17, 2017

(54) PROCESSING OF AUDIO SIGNALS FOR A TINNITUS THERAPY

(71) Applicant: Sonormed GmbH, Hamburg (DE)

(72) Inventors: Marc Adrian Nötzel, Hamburg (DE); Johannes Abraxas Wittig, Braunschweig (DE); Jörg Land, Hamburg (DE); Matthias Lanz, Hamburg (DE)

(73) Assignee: SONORMED GMBH, Hamburg (DE)

( * ) Notice: Subject to any disclaimer, the term of this patent is extended or adjusted under 35 U.S.C. 154(b) by 0 days.

(21) Appl. No.: 14/710,834

(22) Filed: May 13, 2015

(65) Prior Publication Data

US 2015/0245151 A1    Aug. 27, 2015

Related U.S. Application Data

(63) Continuation of application No. PCT/EP2013/003042, filed on Oct. 10, 2013.

(30) Foreign Application Priority Data

Nov. 13, 2012   (DE) ........................ 10 2012 220 620

(51) Int. Cl.
H04R 25/00       (2006.01)
A61B 5/12        (2006.01)
A61M 21/00       (2006.01)

(52) U.S. Cl.
CPC ............... *H04R 25/75* (2013.01); *A61B 5/128* (2013.01); *A61M 21/00* (2013.01); *H04R 25/505* (2013.01); *A61M 2021/0027* (2013.01)

(58) Field of Classification Search
CPC .... H04R 25/75; H04R 25/505; H04R 2225/43
See application file for complete search history.

(56) References Cited

FOREIGN PATENT DOCUMENTS

| DE | 102011001793 A1 | 10/2012 |
|---|---|---|
| WO | 2008087157 A2 | 7/2008 |
| WO | 2011127930 A1 | 10/2011 |

OTHER PUBLICATIONS

PCT International Search Report issued in International Application No. PCT/EP2013/003042, date mailed Dec. 16, 2013, pp. 1-2.

*Primary Examiner* — Matthew Eason
(74) *Attorney, Agent, or Firm* — MKG, LLC

(57) ABSTRACT

A method for processing audio signals in particular for a therapy of subjective tinnitus with an individual tinnitus frequency. The method includes: providing a first audio signal, determining a blocking range in the frequency spectrum of the first audio signal with a predefinable frequency width, creating a second audio signal from the first audio signal using a filter, and determining an auditory energy of the first audio signal or the second audio signal within at least one predefined therapeutically applicable frequency range and specifying an evaluation parameter for the second audio signal.

14 Claims, 5 Drawing Sheets

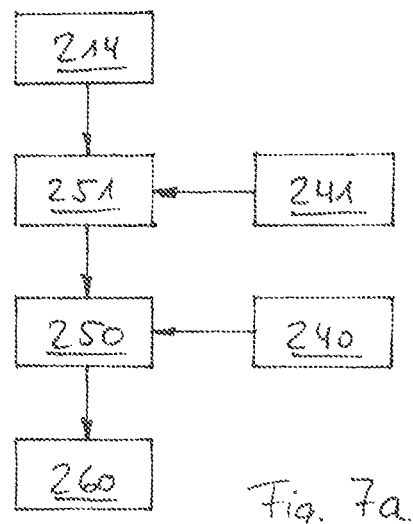
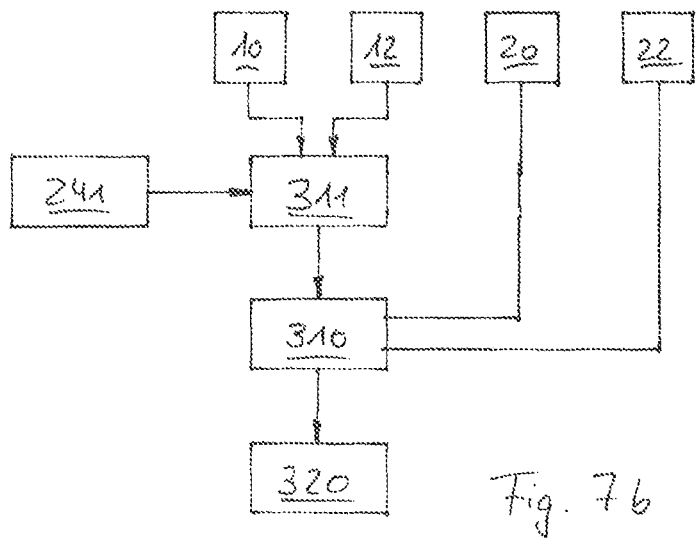

PROCESSING OF AUDIO SIGNALS FOR A TINNITUS THERAPY

CROSS REFERENCE TO RELATED APPLICATIONS

The present application is a continuation application and claims priority benefit under 35 USC §120 to PCT/EP2013/003042, filed on Oct. 10, 2013, which is a PCT application of and claims priority benefit to German Patent Application No. 10 2012 220 620.5 filed on Nov. 13, 2012, the entireties of each of which are incorporated by reference herein.

FIELD

The invention relates to a method for processing audio signals for a therapy of subjective tinnitus with an individual tinnitus frequency. The invention also relates to a computer program.

BACKGROUND

The perception of sounds without the existence of an internal or external sound source is called subjective tinnitus. A tinnitus is an often chronic illness and generally occurs with a constant individual tinnitus frequency. The physiological cause for this is usually an abnormal neuronal activity in the primary auditory cortex.

A possible therapy for relieving a subjective tinnitus is based on the approach of reducing the abnormal neuronal activity in the auditory cortex using lateral inhibition and thereby initiating therapeutically effective normalization of this neuronal activity based on neuronal plasticity.

Lateral inhibition is thereby in particular a characteristic circuitry of the nerve cells in the central nerve system, which causes certain nerve cells to be stimulated in a peripheral stimulus and the activity of different nerve cells is inhibited for the perception of comparable stimuli.

The therapy correspondingly consists of listening to sounds or music, in which the frequency portions were filtered out in the range of the tinnitus frequency. For example, white noise is used for this, from which therapeutic data can be generated for any tinnitus frequencies because white noise has a very broad and even frequency spectrum. White noise is however considered bothersome and unpleasant by the patient in the long run. Willingness to use the therapy regularly and permanently is thereby reduced.

Music is more pleasant to listen to, whereby up until now only professionally produced music with a particularly high audio quality was considered suitable. Since moreover an individual processing for each individual patient is required, a patient generally only has a few different music pieces available for the therapy. These often do not meet the personal tastes of the patient.

SUMMARY

Based on this state of the art, the object of the present invention is to improve the availability of audio data suitable for tinnitus therapy and to enable in particular tinnitus therapy based on audio data selected based on personal tastes.

This object is solved through a method for processing audio signals, in particular for therapy of subject tinnitus with an individual tinnitus frequency, comprising the following method steps:

provision of a first audio signal, determination of a blocking range in the frequency spectrum of the first audio signal with a predefinable frequency width on the basis of a predefinable therapy frequency, creation of a second audio signal from the first audio signal using a filter for a portion of the signal in the first audio signal in the blocking range, determination of an auditory energy of the first audio signal or of the second audio signal within at least one predefined or predefinable therapeutically applicable frequency range specification of an evaluation parameter for the second audio signal as a function of the auditory energy and of a frequency separation between the therapeutically applicable frequency range and the blocking range.

One advantage of the invention is that generally all audio signals come into question as the first audio signal, wherein an objective scale is made available by means of the evaluation parameter, to which extent the second audio signal is suitable for therapy of tinnitus with the individual tinnitus frequency of the present individual case. The second audio signal is then preferably only released or used for tinnitus therapy if the evaluation parameter lies above a predefinable evaluation parameter.

The evaluation parameter is suitably designed in particular to specify how strong the activity of the tonotopic neurons to the therapy frequency or respectively to the blocking range is inhibited by lateral inhibition based on the stimulation of tonotopic neurons to the therapeutically applicable frequency range when listening to the second audio signal. For this, for example knowledge and models of the functionality of the human ear, in particular the lateral inhibition between the neurons of the primary auditory cortex are taken into consideration.

The evaluation parameter is thus in particular an objective scale for how strong the abnormal activity of the neurons causing the tinnitus is inhibited when hearing the second audio signal. Since this is the goal of the tinnitus therapy, the respective evaluation parameter can be determined for example for existing audio signals, which have proven empirically to be suitable or unsuitable in tinnitus therapy, and are specified by comparison with the evaluation parameter determined for the second audio signal, inasmuch as the second audio signal is suitable for the tinnitus therapy.

Another advantage of the invention is that targeted therapeutic control is enabled based on the evaluation parameter. For example, the treating doctor can specify, taking into account the evaluation parameter, how often or how long the second audio signal should be heard for optimal therapeutic success.

The filter used according to the invention is in particular a band-stop filter, through which a portion of the signal of the first audio signal with frequencies in the blocking range is completely or partially removed during creation of the second audio signal. The effect of the band-pass filter should thereby be mainly restricted to the blocking range so that in particular the first audio signal and the second audio signal outside the blocking range mainly match.

The therapeutically applicable frequency range is predefined in particular such that there is no overlap with the blocking range. The auditory energy of the first audio signal within the therapeutically applicable frequency range thus does not mainly differ from that of the second audio signal.

Auditory energy is in particular the sound energy of an audio signal totaled or integrated over all frequencies of a frequency range or of a frequency interval. A frequency range or frequency interval can also be a bandwidth. The auditory energy within a frequency range thus correlates with the strength of a stimulation of the tonotopic neurons at this frequency range.

The method according to the invention is preferably characterized in that the first audio signal and/or the second audio signal is respectively a digital audio signal, in particular a digital audio file or a digital audio data flow.

A digital audio file is in particular a saved digital audio signal, which can be accessed repeatedly and with chronological asynchronism. In contrast, an audio data flow is in particular an audio signal, which is available once and/or with chronological synchronism or in real time.

The first audio signal is preferably normalized before the creation of the second audio signal. The signal-to-noise ratio of the second audio signal is hereby improved and in particular noise effects, which occur during the creation of the second audio signal, in particular during use of the filter, are reduced.

Within the framework of the invention, normalization or controlling is understood in that the first audio signal is scaled such that the highest signal value within the first audio signal corresponds with a predefined maximum value and/or the lowest signal value within the first audio signal corresponds with a predefined minimum value. In the case of digital signals, the maximum value and the minimum value are for example determined by the quantification word width of the first audio signal.

Quantification word width is in particular, in a digital audio signal, the size or word length of the digital information for the coding of a single pulse height value. For example, in a quantification word width of 16 bits, 65536 different discrete values are available for the coding of the pulse height of the audio signal.

It is preferably provided as a further method step that the first audio signal and/or the second audio signal is corrected to compensate for frequency-dependent elevations and/or dampings by a playback device with a non-linear frequency path.

The first audio signal is preferably corrected before or during the creation of the second audio signal. The correction can also be performed during or with the second audio signal.

In this connection, correcting means in particular that frequencies, which are damped due to a non-linear frequency path of the playback device, are correspondingly increased in the audio signal and frequencies, which are increased due to the playback device, are correspondingly damped in the audio signal.

A playback device is in particular a loudspeaker, headphones or a portable or nonportable playback device, for example a stereo system or an mp3 player.

The correcting of the first audio signal (10) or respectively of the second audio signal (12) preferably takes place by means of a filter (121, 120).

The filter coefficients needed for this originate for example from a database, in which filter coefficients for different known playback devices, for example a plurality of procurable headphone models, are stored or saved for repeated use.

A filter used in a method according to the invention is preferably a filter with a finite impulse response. Such filters are also called FIR filters (Finite Impulse Response) or transversal filters. A filter with a finite impulse response can be advantageously implemented as a digital filter and is stable by design. In particular, unwanted oscillations initiated by the filter are thus excluded.

The therapeutically applicable frequency range is preferably analyzed subdivided into frequency intervals, wherein in particular respectively an auditory energy of the first audio signal or of the second audio signal is determined within each frequency interval and the evaluation parameter is determined depending on the respective auditory energy and of a respective frequency distance between the blocking range and the respective frequency interval taking all frequency intervals into consideration. It can thereby be taken into consideration that the lateral inhibition generally decreases with an increasing frequency distance, whereby the correlation between the evaluation parameter and the actual inhibition of neuronal activity is increased. The effort for the analysis in contrast to an analysis of the continuous frequency spectrum is simultaneously considerably reduced through the use of frequency intervals.

The frequency intervals are thereby preferably selected depending on human hearing and have respectively for example a frequency width of ⅓ bark or ⅓ ERB. These two scales are respectively linked non-linearly with the frequency and consider the logarithmic frequency behavior of human hearing over broad ranges.

Furthermore, the first audio signal or respectively the second audio signal is preferably analyzed subdivided into temporally consecutive sections for determining the evaluation parameter, wherein in particular each section comprises a predefinable duration or a predefinable number of digital audio samples. Within the framework of the invention, consecutive sections can be spaced, overlapping or adjacent sections. It is hereby achieved that the evaluation parameter is determined in a time-dependent manner with a temporal resolution, which depends in particular on the duration of a section. In the case of a sampling rate of 44.1 kHz, a section is for example 576 audio samples, whereby a good compromise is achieved between frequency resolution and temporal resolution. The length of the sections can also be designed variably in order to obtain both sections with a high temporal resolution and also sections with a high frequency resolution.

An audio sample is in particular the pulse height information of a digital audio signal at a point in time. The sampling rate or sampling rate thereby specifies in particular the temporal digitalization or discretization of the audio signal, i.e. how many audio samples are coded per time unit in the digital audio signal.

If the first audio signal or respectively the second audio signal has at least two channels, each channel is preferably analyzed individually for determining the evaluation parameter. Phase shifts between the two channels and the corresponding effects on the lateral inhibition of neurons in the auditory cortex can thereby be considered in the determination or calculation of the evaluation parameter.

Alternatively, the evaluation parameter can be determined based on an individual channel or from a mixed signal of several channels. This is in particular advantageous when analysis effort is time-critical, for example in real-time applications of the method according to the invention.

A method according to the invention is particularly preferably executed using a data processing device.

The data processing device is designed in particular for the digital processing of analog and/or digital audio signals, wherein analog audio signals are digitized for example by means of data processing device before executing the method according to the invention.

A suitable data processing device is for example a server, a multimedia computer or a laptop, which have the advantage of being accessible to anyone.

Preferably, the data processing device is or will be connected with a playback device by means of a first data connection, wherein the second audio signal is transferred by the data processing device to the playback device via the first data section.

A playback device is in particular designed to play back audio signals and is for example a computer or laptop, a smartphone or a mobile playback device.

Suitable data connections are for example provided via a network, like Ethernet, LAN (Local Area Network) or WLAN (Wireless Local Area Network), via standard interfaces like Bluetooth, USB (Universal Serial Bus) or infrared or as telecommunications connection like ISDN, DSL, GSM or UMTS.

Preferably, the data processing device is or will be connected with a data storage device by means of a second data connection, wherein the first audio signal is transferred by the data storage device to the data processing device via the second data section.

The invention also expressly comprises such embodiments, in which the playback device is designed as a data storage device. In this case, the first data connection and the second data connection can be produced in particular identically or produced in succession temporally.

The first data connection and/or the second data connection is or will be or respectively are or will be preferably produced via a data network, in particular via the Internet.

Regardless of the format of the first audio signal, the second audio signal is for example an audio file, which is made available for access or download via the data network. The second audio signal can also be an audio data flow, which is transferred to the playback device in real time via the data network.

The object underlying the invention is further solved by a computer program product with program code means, which are designed to execute a method according to the invention when the program code means is executed on a data processing device.

The program code means are preferably saved on a data storage medium readable by a computer. This can hereby be a CD, a disk, a hard drive or even storage space on a server. The saving can be provided both in a RAM or ROM or a solid-state memory or fixed-disk memory on a server.

Within the framework of the invention, in particular also program code means, which are saved on an Internet server and offered as download for the temporary or permanent saving, installation and/or use on a computer or laptop, are understood as computer program products.

The object based on the invention is also solved by a computer system with a data processing device, which is set up to execute the method according to the invention.

For this, the computer system comprises for example program code means, which are designed to execute a method according to the invention when the program code means are executed on the data processing device. Alternatively or supplementary, the data processing device has suitable components, for example electronic circuits or microelectronic components, for executing individual or all method steps.

Further characteristics of the invention will become apparent from the description of embodiments according to the invention together with the claims and the included drawings. Embodiments according to the invention can fulfill individual characteristics or a combination of several characteristics.

BRIEF DESCRIPTION OF THE DRAWINGS

The invention is described below, without restricting the general idea of the invention, using exemplary embodiments with reference to the drawings, whereby we expressly refer to the drawings with regard to all details according to the invention that are not explained in greater detail in the text. The figures show in:

FIG. 7a is schematically a section of a flow chart of a filter of a method according to the invention and FIG. 7b is schematically a section of a flow chart of a method according to the invention.

In the drawings, the same or similar types of elements and/or parts are provided with the same reference numbers so that a re-introduction is omitted.

DETAILED DESCRIPTION

Figure 1:
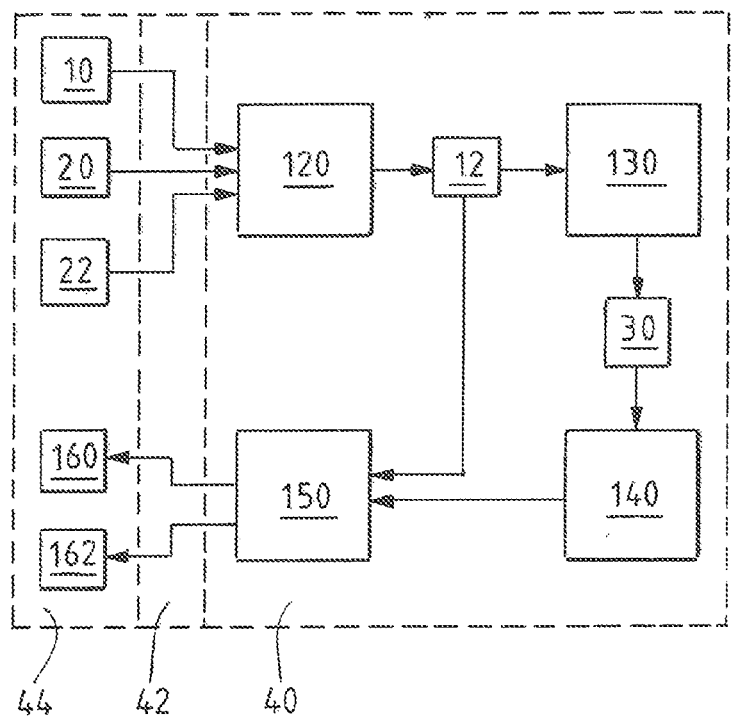
FIG. 1 is schematically an exemplary implementation of a method according to the invention.

An exemplary implementation of the method according to the invention is shown in FIG. 1. A server 40 is thereby provided, which is accessible for example via a corresponding web front end via the Internet 42 by a client computer 44.

Via the client computer 44, an original audio signal 10, for example an audio file saved on the client computer 44, is transferred to the server 40 via the Internet 42, where a therapy signal 12 is created by means of a digital filter 120. For the configuration of the filter, an individual tinnitus frequency 20 or therapy frequency 20 and optionally a blocking range 22, in particular blocking range width, are provided via the client computer 44, which have been determined for example by the treating doctor for the individual tinnitus patient. If no blocking range 22 is specified, a standard value, for example an octave, is used for the blocking range 22.

In a signal analysis 130, the therapy 12 is analyzed and at least one evaluation parameter 30 is determined. On the basis of significance of being a measure for the inhibition of the neuronal activity, the evaluation parameter 30 is also called inhibition parameter 30 in the following.

In a parameter evaluation 140, the inhibition parameter 30 is compared with reference parameters in order to determine the suitability of the therapy signal 12 for the therapy or treatment of the individual tinnitus with the tinnitus frequency 20.

The reference parameters are based for example on reference signals, which have proven to be suitable or unsuitable for tinnitus therapy in empirical studies, wherein the reference parameters are specified by the inhibition 30 for the reference signals determined by means of the signal analysis 130.

The result of the parameter evaluation 140 is transmitted to the client computer 44 via a user dialog 150. The user dialog 150 simultaneously provides an audio data flow 160 with the therapy signal 12 for playback by means of the client computer 44 or an audio file 162 with the therapy signal 12 for storage on the client computer 44.

Figure 2:
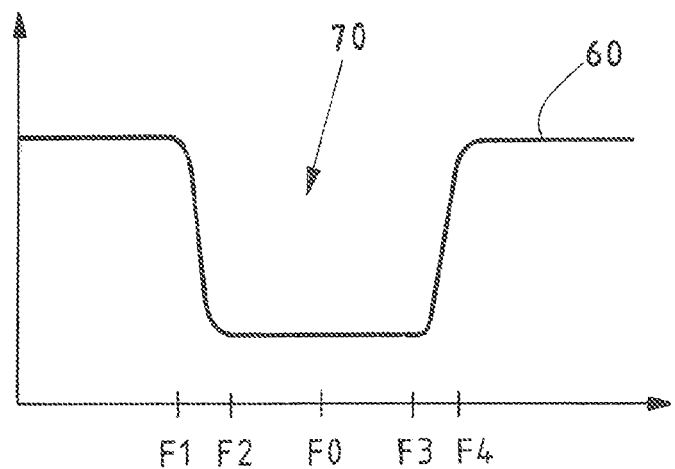
FIG. 2 is schematically the amplitude frequency response of a used filter according to the invention.

The amplitude frequency path of the filter 120 is represented schematically in FIG. 2 in the form of a characteristic curve 60. The horizontal axis of the frequency of the audio signal to be filtered and the vertical axis of the damping of the filter thereby match.

The characteristic curve 60 of the filter 120 has a band-stop filter 70 around a center frequency F0, which corresponds in particular with the individual tinnitus frequency 20. The band-stop filter 70 has a therapeutic goal range or blocking range with a blocking range 22, which is for example an octave or is specified as variable blocking width 22. The blocking range defines a lower threshold frequency F2 of the therapeutic target range or respectively blocking range and an upper threshold frequency F3 of the therapeutic target range or respectively blocking range, wherein the blocking range is arranged for example on a logarithmic frequency scale symmetrically around the center frequency F0. The damping of the band-stop filter 70, in particular the damping of the filter in the therapeutic target range, is determined in particular depending on the quantification word width M of a digital audio signal to be filtered 10 and is for example M*6 dB+2 dB.

Above and below the blocking range, the band-stop filter 70 has transition areas, which are characterized by the lower threshold frequency F1 of the band-stop filter 70 and the upper threshold frequency F4 of the band-stop filter 70. The width of the transition areas is thereby dependent on the implementation of the respective filter 120, wherein a decreasing width of the transition areas in the case of a digitally implemented filter 120 is generally connected with increased computing effort and thus with increased time effort during the creation of the therapy signal 12. The filter 120 is preferably designed or configured such that the width of the transition areas is small compared to the blocking range 22. For example, each of the widths of the transition areas is a quarter tone when the blocking range 22 is one octave or respectively six whole tone steps.

Outside of the transition areas, each characteristic curve 60 of the filter 120 has passbands, in which the audio signal to be filtered mainly remains unchanged. In these areas, the damping is correspondingly zero.

Figure 3:
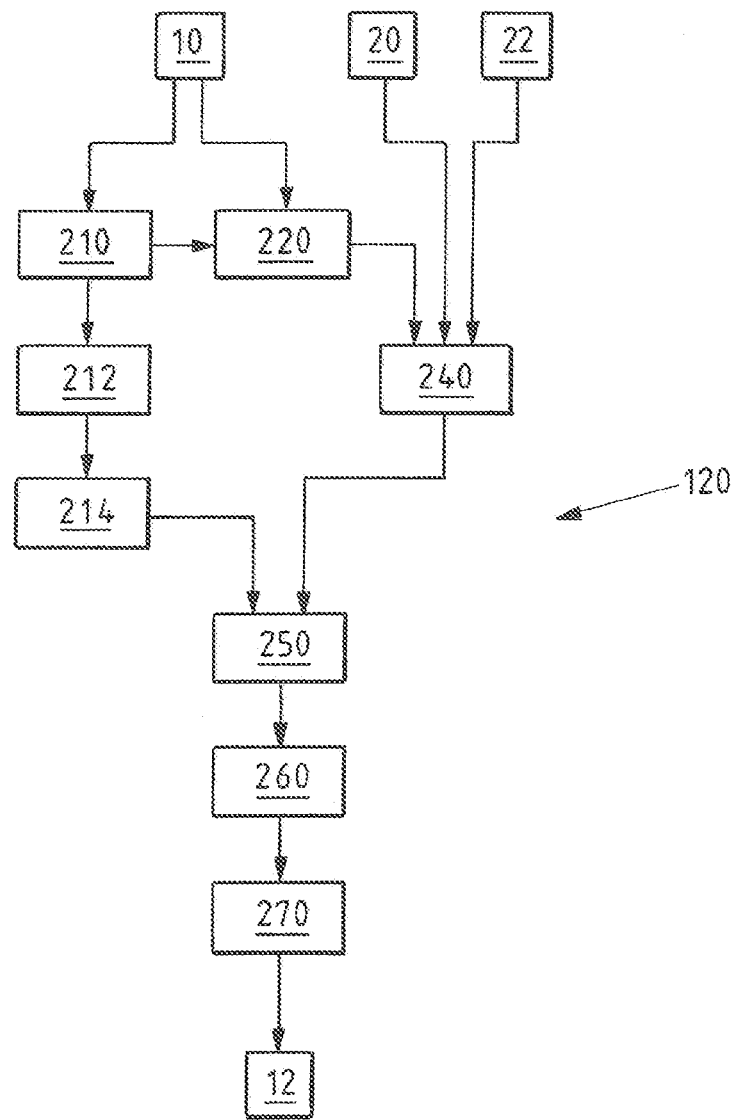
FIG. 3 is schematically a flow chart of a filter of a method according to the invention.

FIG. 3 shows an exemplary implementation of the digital filter 120. Input parameters for the filter 120 are the original audio signal 10, which is in particular one digital audio signal, the individual tinnitus frequency 20 as well as the blocking range 22.

In a signal preparation 210, the original audio signal 10 is decoded and, if applicable, converted to a linear PCM format (Pulse Code Modulation) if the original audio signal 10 is not yet available in such a format.

The audio signal prepared in this manner undergoes a normalization 212 in order to keep the signal-to-noise ratio of the filtered audio signal low. If the step response of the filter 120 produces overshoots, the audio signal is also reduced approximately by the height of the overshoot in a linear damping 214 in order to avoid distortions in the filtered audio signal.

Furthermore, the sampling rate of the audio signal 10 as well as the quantification word width M of the prepared audio signal are determined in a parameter determination 220.

The actual filtering of the audio signal takes place by means of an FIR filter 250 through numeric folding with suitable filter coefficients, which were determined previously taking into consideration the sampling rate, the quantification word width M, the individual tinnitus frequency 20 as well as the blocking range 22 (block 240).

In a subsequent noise suppression 260, the so-called dithering, digitalization roundings are randomized in the filtered audio signal. In a signal post-processing 270, the filtered audio signal is then converted to a freely selectable data format and made available as a therapy signal 12. For example, the data format of the original audio signal 10 is used.

Figure 4:
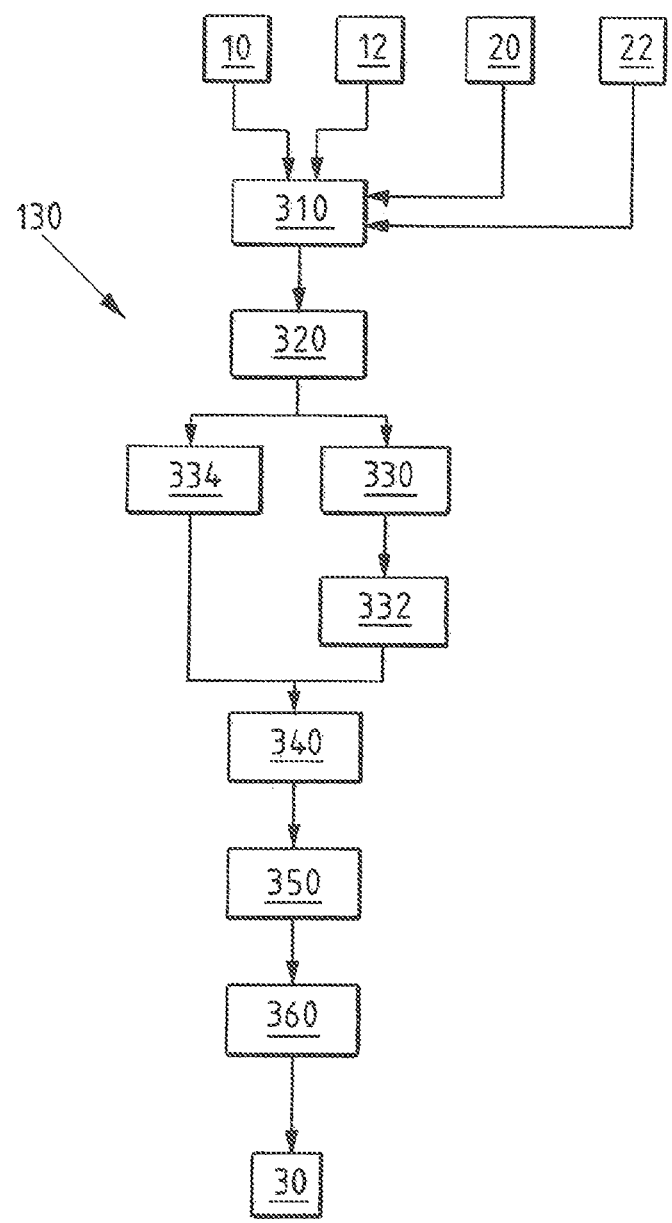
FIG. 4 is schematically a flow chart of a signal analysis of a method according to the invention.

FIG. 4 shows schematically a flow chart of an exemplary implementation of the signal analysis 130. On the input side, the original audio signal 10 or the therapy signal 12, the tinnitus frequency 20 as well as the blocking range 22 are supplied to the signal analysis 130.

The audio signal 10, 12 to be analyzed is analyzed in sections, wherein one section comprises for example 576 audio samples at a sampling rate of 44.1 kHz and is called a granule below. Moreover, if present, the left stereo channel and the right stereo channel of the audio signal can be analyzed individually.

Each granule of the audio signal 10, 12 to be analyzed is analyzed in the frequency range on the basis of the functionality of human hearing. The modeling of human hearing is generally based on auditory filters with a different and usually relative bandwidth. These are for example the frequency groups according to Zwicker, i.e. the so-called bark scale, or the equivalent rectangular bandwidth, i.e. the so-called ERB scale (Equivalent Rectangular Bandwidth) according to Moore. Both the bark scale and the ERB scale are linked with the frequency non-linearly and selected such that the division of the scale into integer scale sections corresponds with the signal processing of human hearing. For a differentiated analysis, each scale section can respectively be divided into several, for example three, parts. Such a part is called a partition band below and has for example a width of ⅓ bark or ⅓ ERB.

In each granule of the audio signal 10, 12 to be analyzed, an auditory energy contained in the partition band is determined for each partition band (block 310). This takes place for example using a Fast Fourier Transformation, FFT, and assuming a sound pressure level, which leads to a volume that is considered moderate when listening to the audio signal 10, 12. For example, the audio signal 10, 12 to be analyzed is thereby scaled such that the maximum sound pressure level is approximately 70 dB.

Furthermore, a tonality is determined for each partition band in each granule (block 320). The tonality is a measure for whether a sound event is noise-like, i.e. wide-band, or tonal, i.e. narrow-band. It can be determined for example via the predictability or periodicity of the audio signal over time, wherein an observation of several successive temporal sections of the audio signal 10, 12 to be analyzed is required. Alternative determination processes, for example based on the distribution of the sound energy in the frequency spectrum of the actually analyzed granule, in particular within the individual partition bands of the granule, are thus preferred.

If the actual partition band lies in full or in part outside of the therapeutic target range, then an excitation strength of the actual partition band determines an excitation strength first based on the auditory energy and the tonality (block 330), wherein it can be taken into consideration that noise-like sound events are perceived stronger or louder than tonal sound events at the same sound pressure. It can also be taken into consideration that higher frequencies are perceived weaker or less loud than deeper tones at the same sound energy in that for example the excitation strength is reduced when the actual partition band lies above the tinnitus frequency 20 or respectively above the therapeutic target range.

The excitation strength is a measure for the stimulation of the neurons of the primary auditory cortex tonotopic to the actual partition band.

A damping strength is determined from the excitation strength for the actual partition band for all other partition bands (block 332), which is a measure for the lateral inhibition of the neurons respectively tonotopic to the other partition bands. In particular neuroacoustic or psychoacoustic spreading functions are used for this in particular. It is thereby taken into consideration in particular that the range of the lateral inhibition depends greatly on the excitation strength or the strength of the stimulation of the neurons tonotopic to the actual partition band. The greater the excitation strength, the greater the frequency range or respectively the number of neighboring partition bands, in which the lateral inhibition shows relevant effects. If empirically psychoacoustic spreading functions are used, a correction based on the frequency curves of the same volume (isophones) according to ISO 226:2003 thus preferably takes place in order to compensate in particular for frequency-evaluating properties of the outer, middle and inner ear.

If the actual partition band lies within the therapeutic target range, which is defined in particular by the tinnitus frequency 20 and the blocking range 22, an excitation strength is also determined (block 334). It is thereby then differentiated whether the audio signal 10, 12 to be analyzed is an unfiltered or original audio signal 10 or a therapy signal 12.

In the case of an unfiltered audio signal 10, the excitation strength is set to zero. The unfiltered audio signal 10 is treated correspondingly as if it had been processed with an ideally damping band-stop filter with infinitely narrow transition areas.

In the case of a filtered audio or a therapy signal 12, the excitation strength as in the case of a partition band is determined outside the therapeutic target range or respectively blocking range.

The analysis steps 310, 320, 330, 332, 334 described above are repeated for all partition bands of a granule. An excitation strength and a plurality of damping strengths are then available for each partition band of the granule.

The damping strengths for each partition band are combined respectively into a total damping strength for this partition band (block 340). This takes place for example by means of intensity addition, by means of non-linear addition or by means of maximum value calculation.

Optionally, the excitation strengths and the total damping strengths of all partition bands of a granule are corrected with respect to such one or more other granules (block 350).

Through a correction with respect to one or more preceding granules, it can be taken into consideration for example that a strong excitation or damping of a neuronal areal continues to have an effect for a short time even after fading of the stimulus.

Accordingly, it can be taken into consideration through correction with respect to a simultaneous granule for another channel of the audio signal 10, 12 that, if applicable, an excitation of the neurons responsible for an ear results in a damping of the neurons responsible for the other ear.

The total damping strengths of those partition bands lying within the therapeutic target range are subsequently combined into an inhibition parameter 30 (block 360), which takes place for example by means of intensity addition, by means of non-linear addition or by means of maximum value calculation. If the audio signal to be analyzed is a therapy signal 12, the excitation strengths of the partial bands lying within the blocking range with the opposite sign are also included.

An inhibition parameter 30 is thus then available for each granule, which is a measure for an inhibition of neuronal activity in the primary auditory cortex of the actual granule of the analyzed therapy signal 12 or respectively of a therapy signal created from the analyzed unfiltered audio signal 10.

Additional parameters, which also correlate with the inhibition of neuronal activity in the primary auditory cortex, can be determined from the inhibition parameters 30.

In particular, the simultaneous granules of the two stereo channels can be combined into a sum parameter and into a difference parameter. The sum parameter, for which the inhibition parameters 30 of the granules of both stereo channels are considered in particular with the same signs, is for example a measure for the therapy potential of the audio signal 10, 12. This also applies if the therapy takes place by means of a loudspeaker and thus both ears are both equally exposed to the two stereo channels. The difference parameter, for which the inhibition parameters 30 of the granules of both stereo channels are considered in particular with different signs, specifies in contrast how the therapy potential of the audio signal 10, 12 is distributed to the stereo channels. This is interesting in particular for when the therapy takes place with headphones and thus each ear is exposed to one stereo signal.

The inhibition parameters 30, the sum parameters or the difference parameters of all granules of an audio signal 10, 12 can also be combined into one total parameter, which accordingly specifies in particular the therapeutic potential of the total audio signal 10, 12. This takes place for example by means of intensity addition, non-linear addition, maximum value formation or even average value formation.

Figure 5:
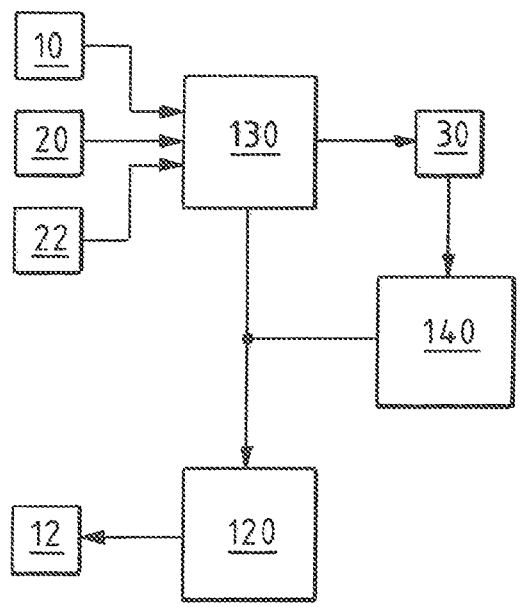
FIG. 5 is schematically a further exemplary implementation of the method according to the invention.

FIG. 5 shows schematically a further implementation of the method according to the invention, which differs from the implementation according to FIG. 1 in that the signal analysis 130 is first performed and the inhibition parameter 30 is determined. It is then evaluated in the parameter evaluation 140, wherein the therapy signal 12 only takes place by means of the filter 120 when the parameter evaluation 140 has produced sufficient therapeutic suitability of the original audio signal 10.

The implementations according to FIG. 1 and FIG. 5 can also be combined, wherein the signal analysis 130 is then executed both on the original audio signal 10 as well as on the therapy signal 12.

Figure 6:
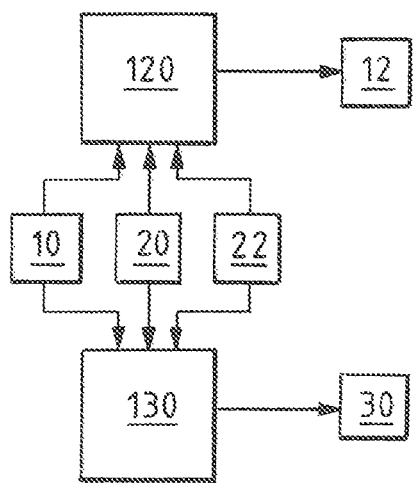
FIG. 6 is schematically another exemplary implementation of the method according to the invention.

FIG. 6 shows a further embodiment of the method according to the invention, which is suitable in particular for real-time applications. The filter 120 and the signal analysis 130 are hereby executed in parallel so that the therapy signal 12 and the inhibition parameter 30 are available simultaneously.

The method according to the invention is also suitable for preparing or processing audio signals for a tinnitus therapy for use with playback device that have a non-linear frequency path.

For example, commercially available headphones often have a non-linear frequency path due to their design or manipulated in a targeted manner, wherein the non-linearity is generally homogeneous for all models of a series and is correspondingly known or at least determinable.

Through use of a non-linear playback device or a playback device with non-linear frequency path, the therapeutic qualities of the audio signal provided for tinnitus therapy are reduced and the assessment of the therapeutic suitability of the audio signal is falsified according to the above description.

In order to prevent this, an optional correction of the audio signal provided for the therapy is provided within the framework of the invention. An exemplary design of this correction is described in FIGS. 7a and 7b.

FIG. 7a shows schematically a section of a flow chart of a filter 120 for a method according to the invention. The filter 120 corresponds with the filter 120 shown in FIG. 3, wherein the section shown in FIG. 7a replaces the blocks 214, 240 and 250 in FIG. 3.

In front of the FIR filter 250, a further correction filter 251, designed for example as an FIR filter, is used, by means of which a correction is performed with respect to the non-linearity of the playback device. For example, filter coefficients 241 or correction coefficients 241 from a database are used for this, which are adjusted to the playback device to be corrected. Such frequencies, which are played back in a damped manner due to the non-linearity of the playback device, are increased by the correction filter 251 in the filtered audio signal. Such frequencies, which are played back excessively or strengthened due to the non-linearity of the playback device, are correspondingly damped in the filtered audio signal.

The occurring correction in the audio signal 12 provided for the therapy is also preferably taken into consideration in the determination of the inhibition parameter 30, as shown in FIG. 7b. FIG. 7b shows a section of a flow chart comparable with FIG. 4, wherein for example the upper part of the representation in FIG. 4 is replaced by the section in FIG. 7b.

A non-linearity simulation 311 is performed here before the determination of the auditory energy (block 310), in order to correctly consider the non-linearity of the playback device. The non-linearity simulation 311 is thereby based on the correction coefficient 241 already used for the correction filter 251.

All named characteristics, including those taken from the drawings alone and also individual characteristics, which are disclosed in combination with other characteristics, are considered alone and in combination as essential for the invention. Embodiments according to the invention can be realized by individual characteristics, or a combination of several characteristics.

What is claimed is:

1. A method for processing audio signals (10, 12), for a therapy of subjective tinnitus with an individual tinnitus frequency, the method comprising:
   provision of a first audio signal (10),
   determination of a blocking range in a frequency spectrum of the first audio signal (10) with a predefinable frequency width (22) on the basis of a predefinable therapy frequency (20);
   creation of a second audio signal (12) from the first audio signal (10) using a filter (120, 121) for a portion of the signal in the first audio signal (10) in the blocking range;
   determination of an auditory energy of the first audio signal (10) or of the second audio signal (12) within at least one predefined or predefinable therapeutically applicable frequency range; and
   specification of an evaluation parameter (30) for the second audio signal (12) as a function of the auditory energy and of a frequency separation between the therapeutically applicable frequency range and the blocking range,
   wherein the therapeutically applicable frequency range is analyzed subdivided into frequency intervals, wherein in particular respectively an auditory energy of the first audio signal (10) or of the second audio signal (12) is determined within each frequency interval and the evaluation parameter (30) is determined depending on the respective auditory energy and of a respective frequency distance between the blocking range and the respective frequency interval taking all frequency intervals of the therapeutically applicable frequency range into consideration.

2. The method according to claim 1, wherein at least one of the first audio signal (10) and the second audio signal (12) are respectively a digital audio signal, in particular a digital audio file or a digital audio data flow.

3. The method according to claim 1, wherein the first audio signal (10) is normalized before the creation of the second audio signal (12).

4. The method according to claim 1, wherein at least one of the first audio signal (10) and the second audio signal (12) is corrected to compensate for at least one of frequency-dependent elevations and dampings by a playback device with a non-linear frequency path.

5. The method according to claim 4, wherein the correction of the first audio signal (10) and the second audio signal (12) is carried out by means of a filter (121, 120).

6. The method according to claim 1, wherein a used filter (120, 121) is a filter with finite impulse response.

7. The method according to claim 1, wherein the first audio signal (10) or respectively the second audio signal (12) has at least two channels, wherein each channel is analyzed individually for determining the evaluation parameter (30).

8. The method according to claim 1, wherein the method is performed using a data processing device (40).

9. The method according to claim 8, wherein the data processing device (40) is connected with a playback device (44) by means of a first data connection, wherein the second audio signal (12) is transmitted by the data processing device (40) to the playback device (44) via the first data connection.

10. The method according to claim 8, wherein the data processing device (40) is connected with a data storage device (44) by means of a second data connection, wherein the first audio signal (10) is transmitted by the data storage device (44) to the data processing device (40) via the second data connection.

11. The method according to claim 9, wherein at least one of the first data connection and the second data connection is or will be established via a data network (42).

12. A computer program product with program code means, the program code means being designed to execute a method according to claim 1 when the program code means are executed on a data processing device (40).

13. A computer system with a data processing device (40), which is set up to execute a method according to claim 1.

14. A method for processing audio signals (10, 12), for a therapy of subjective tinnitus with an individual tinnitus frequency, the method comprising:
   provision of a first audio signal (10),
   determination of a blocking range in a frequency spectrum of the first audio signal (10) with a predefinable frequency width (22) on the basis of a predefinable therapy frequency (20);

creation of a second audio signal (12) from the first audio signal (10) using a filter (120, 121) for a portion of the signal in the first audio signal (10) in the blocking range;

determination of an auditory energy of the first audio signal (10) or of the second audio signal (12) within at least one predefined or predefinable therapeutically applicable frequency range; and specification of an evaluation parameter (30) for the second audio signal (12) as a function of the auditory energy and of a frequency separation between the therapeutically applicable frequency range and the blocking range, wherein the first audio signal (10) or the second audio signal (12) is analyzed subdivided into temporally consecutive sections for determining the evaluation parameter (30), wherein in particular each section comprises a predefinable duration or a predefinable number of digital audio samples.

* * * * *